United States Patent [19]

Curatolo

[11] Patent Number: 5,030,452
[45] Date of Patent: Jul. 9, 1991

[54] DISPENSING DEVICES POWERED BY LYOTROPIC LIQUID CRYSTALS

[75] Inventor: William J. Curatolo, Groton, Conn.

[73] Assignee: Pfizer Inc., New York, N.Y.

[21] Appl. No.: 296,458

[22] Filed: Jan. 12, 1989

[51] Int. Cl.$^5$ .............................................. A61K 37/22
[52] U.S. Cl. ..................................... 424/450; 424/451; 424/452; 424/463; 424/473; 428/1
[58] Field of Search ............... 424/450, 463, 451, 452, 424/473; 264/4.6; 428/1

[56] References Cited

U.S. PATENT DOCUMENTS

| | | | |
|---|---|---|---|
| 3,538,214 | 11/1970 | Polli | 424/19 |
| 3,845,770 | 11/1974 | Theeuwes et al. | 128/260 |
| 3,995,631 | 12/1976 | Higuchi et al. | 128/260 |
| 4,111,202 | 12/1978 | Theeuwes | 128/260 |
| 4,160,020 | 7/1979 | Ayer, et al. | 424/15 |
| 4,180,073 | 12/1979 | Michaels | 128/260 |
| 4,217,898 | 8/1980 | Theeuwes | 128/260 |
| 4,327,725 | 5/1982 | Cortese et al. | 128/260 |
| 4,350,271 | 9/1982 | Eckenhoff | 222/386.5 |
| 4,439,196 | 3/1984 | Higuchi | 604/890 |
| 4,449,983 | 5/1984 | Cortese et al. | 604/892 |
| 4,608,048 | 8/1986 | Cortese et al. | 604/890 |
| 4,615,698 | 10/1986 | Guittard et al. | 604/892 |
| 4,627,971 | 12/1986 | Ayer | 424/15 |
| 4,666,704 | 5/1987 | Shalati et al. | 424/19 |
| 4,673,405 | 6/1987 | Guittard et al. | 604/890 |
| 4,678,467 | 7/1987 | Eckenhoff et al. | 604/892 |
| 4,684,524 | 8/1987 | Eckenhoff et al. | 424/469 |
| 4,761,288 | 8/1988 | Mezei | 424/450 |
| 4,765,989 | 8/1988 | Wong et al. | 424/473 |
| 4,772,474 | 9/1988 | Eckenhoff et al. | 424/465 |
| 4,783,337 | 11/1988 | Wong et al. | 424/468 |
| 4,784,858 | 11/1988 | Ventouras | 424/468 |
| 4,857,336 | 8/1989 | Khanna et al. | 424/473 |
| 4,859,470 | 8/1989 | Guittard et al. | 424/473 |
| 4,902,514 | 2/1990 | Barclay et al. | 424/473 |

FOREIGN PATENT DOCUMENTS

| | | |
|---|---|---|
| 169105 | 1/1986 | European Pat. Off. . |
| 190969 | 6/1986 | European Pat. Off. . |
| 233009 | 8/1987 | European Pat. Off. . |
| 248447 | 12/1987 | European Pat. Off. . |
| 250374 | 12/1987 | European Pat. Off. . |
| 253541 | 1/1988 | European Pat. Off. . |
| 277092 | 8/1988 | European Pat. Off. . |
| 3629994 | 3/1986 | Fed. Rep. of Germany . |
| 2140687 | 12/1984 | United Kingdom . |
| 2150830 | 7/1985 | United Kingdom . |
| 2155787 | 10/1985 | United Kingdom . |
| 2189995 | 4/1987 | United Kingdom . |
| 2193632 | 2/1988 | United Kingdom . |

OTHER PUBLICATIONS

S. Janicki, et al., "Gastrointestinal Therapeutic System Delivering of a Water Insoluble Drug: Isosorbide Dinitrate (ISDN)", Pharmazie 42:95–96 (1987).

T. Gulik-Krzywicki et al., "The Smectic Phase of Lipid-Water Systems: Properties Related to the Nature of the Lipid and to the Presence of Net Electrical Charges", Molecular Crystals and Liquid Crystals, 8:285–291 (1969).

M. J. Janiak et al., "Temperature and Compositional Dependence of the Structure of Hydrated Dimyristoyl Lecithin", J. Biol. Chem. 254:6068–6078 (1979).

G. G. Shipley, Chapter 1, Biological Membranes, vol. II, D. Chapman, Ed., Academic Press, N.Y. (1973) pp. 1–19.

D. M. LeNeveu et al., "Measurement of Forces Between Lecthin Bilayers", Nature 259:601–603 (1976).

Primary Examiner—Merrell C. Cashion, Jr.
Assistant Examiner—P. L. Prater
Attorney, Agent, or Firm—Peter C. Richardson; J. Trevor Lumb; A. Dean Olson

[57] ABSTRACT

This invention relates to devices useful for the controlled delivery of one or more beneficial agents to an environment of use. More specifically, this invention concerns such devices which are powered by lyotropic liquid crystals. This inventioin also relates to the controlled delivery of one or more beneficial agents to an aqueous environment of use through the use of such lyotropic liquid crystal powered dispensing devices. Also disclosed are methods for the controlled delivery of one or more beneficial agents to an aqueous environment of use which comprise administering to or otherwise placing the devices of this invention in the environment of use.

19 Claims, 4 Drawing Sheets

DISPENSING DEVICES POWERED BY LYOTROPIC LIQUID CRYSTALS

BACKGROUND OF THE INVENTION

1. Field of the Invention

This invention relates to devices useful for the controlled delivery of one or more beneficial agents to an environment of use. More specifically, this invention concerns such devices which are powered by lyotropic liquid crystals. This invention also relates to the controlled delivery of one or more beneficial agents to an aqueous environment of use through the use of such lyotropic liquid crystal powered dispensing devices. Further, still, this invention is concerned with devices for the controlled delivery of one or more beneficial agents to the physiological fluid of animals including mammals such as human beings.

2. General Background of the Invention

The desirability of controlled release of beneficial agents into an environment of use such as the physiological fluid of animals including mammals such as human beings is well known to those skilled in the relevant art. Controlled delivery of beneficial agents such as drugs can, for example, result in a relatively constant concentration of such agents in the physiological fluids of an animal instead of the more dramatic rises and subsequent decreases in concentration of such agents usually associated with periodic dosing. Furthermore, controlled delivery of drugs can eliminate certain deleterious effects sometimes associated with a sudden, substantial rise in the concentration of certain drugs.

A variety of devices for the controlled delivery of beneficial agents have been described. Certain of those devices employ the physical phenomenon of diffusion for their operation. Examples of such diffusion driven devices are disclosed in U.S. Pat. No. 4,217,898. Other devices have been described which operate with the principle of colloidal osmotic pressure. Examples of such osmotically driven devices are disclosed in U.S. Pat. Nos. 3,845,770; 3,995,631; 4,111,202; 4,160,020; 4,439,196 and 4,615,698. Devices which employ a swellable hydrophilic polymer which polymer exerts pressure on a container and thereby forces drug therefrom is disclosed in U.S. Pat. No. 4,180,073. U.S. Pat. No. 4,327,725 discloses a device which employs a layer of fluid swellable hydrogel to force beneficial agent out of the device through a specified and defined passageway. Other hydrogel powered devices containing such a passageway for delivery of beneficial agents are disclosed in GB 2,140,687A.

Applicant's copending application, assigned to the assignee thereof and filed concurrently herewith entitled "Dispensing Devices Powered by Hydrogel" bearing applicant's docket number PC7541/GCB, discloses dispensing devices, powered by hydrogel, for the controlled delivery of one or beneficial agents to an environment of use.

It is a object of this invention to provide devices for the controlled delivery of one or more beneficial agents to an environment of use. Another object of this invention is to provide devices powered by lyotropic liquid crystals which will effect the controlled delivery of one or more beneficial agents to an aqueous environment of use. Yet another object of this invention is to provide devices powered by lyotropic liquid crystals for the controlled delivery of one or more beneficial agents to the physiological fluids of an animal including a human being. This invention also has as an object the provision of a device to controllably deliver one or more beneficial agents which are insoluble or substantially insoluble in water or physiological fluids. Another object still of this invention is to provide devices powered by lyotropic liquid crystals which do not require a semipermeable coating, but instead can employ a coating which is permeable to the beneficial agent. Further still, it is an object of this invention to provide devices powered by lyotropic liquid crystals which can assume a variety of shapes and sizes and devices which can be delivered to an environment of use in a capsule.

It is also an object of this invention to provide methods for the controlled delivery of one or more beneficial agents to an environment of use by administering to or otherwise placing the device of this invention into the environment.

These and other objects of this invention will be readily apparent to those skilled in the relevant art enabled by the disclosure herein.

SUMMARY OF THE INVENTION

This invention concerns devices for the controlled delivery of one or more beneficial agents to an environment of use which devices comprise a mixture of one or more beneficial agents and lyotropic liquid crystals surrounded by a coating of a material that is permeable to water and/or aqueous medium such as physiological fluid and which coating contains one or more holes and/or a plurality of pores.

This invention also concerns devices for the controlled delivery of one or more beneficial agents to an aqueous environment of use which devices comprise two adjacent layers, the first layer comprising a mixture of one or more beneficial agents and lyotropic liquid crystals; and the second layer comprising lyotropic liquid crystals of the same or different composition as the lyotropic liquid crystals in the first layer. Such devices have a coating comprising a material which is permeable to water and/or aqueous medium and which contains one or more holes and/or a plurality of pores such as the devices described above.

All of the devices of this invention optionally can include therein one or more excipients and/or osmotically effective solutes.

In a preferred embodiment of this invention, the lyotropic liquid crystals are comprised of phospholipids and/or salts of fatty acids and the coating material is comprised of cellulose acetate.

This invention also relates to capsules which contain one or more of the devices as described above.

Further, this invention concerns methods for the controlled delivery of one or more beneficial agents to an aqueous environment of use which comprises administering to or otherwise placing the devices and/or the capsules of this invention in the environment of use.

DETAILED DESCRIPTION OF THE DRAWINGS

FIGS. 1–8 depict certain embodiments of the devices of this invention and are meant to be illustrative of such embodiments of the invention herein. The Figures are not to be construed as limiting in any way the scope of this invention to the embodiments depicted therein. Further, the various components of the devices depicted in the Figures are representational and are not necessarily drawn to scale.

Figure 1:
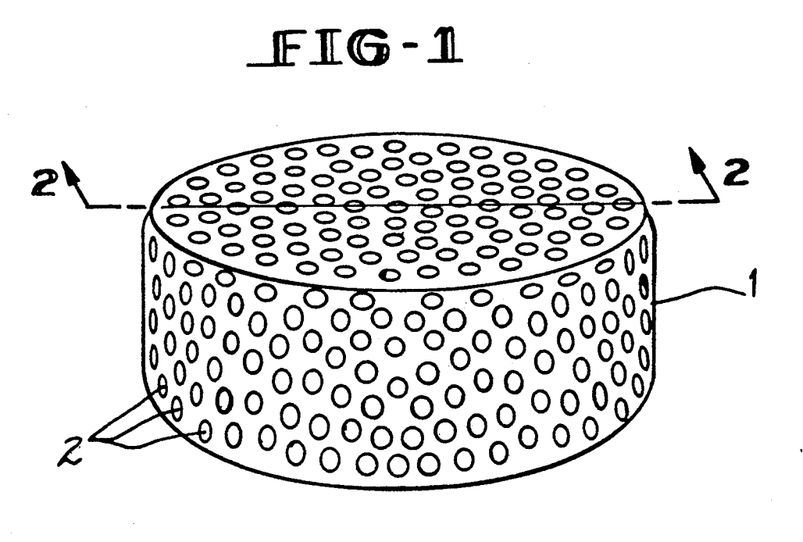
FIG. 1 is a perspective view of one embodiment of the device (1) of this invention in the shape of a tablet.

FIG. 1 shows one embodiment of the device (1) of this invention in the form of a tablet containing a plurality of pores (2).

Figure 2:
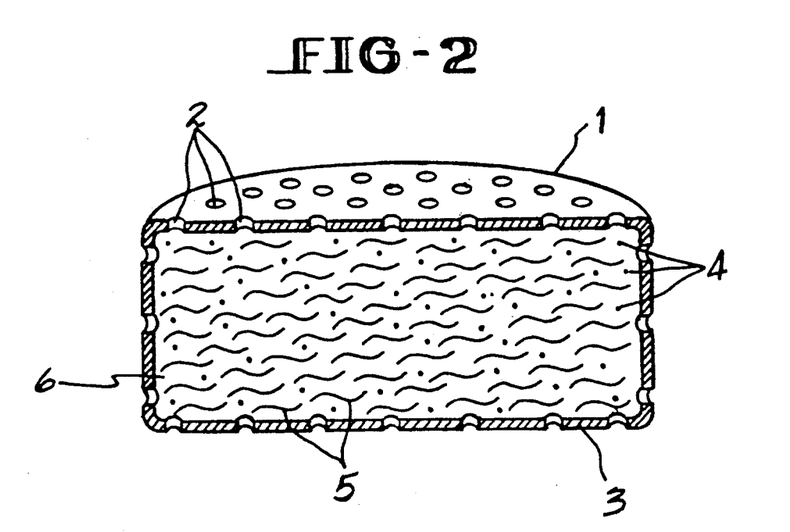
FIG. 2 is a cross-sectional view taken along line 2—2 of the, device (1) shown in FIG. 1.

FIG. 2 is a cross-sectional view taken along line 2—2 of FIG. 1 and shows the coating (3) of the device (1) which contains a plurality of pores (2) in and through the coating (3). A mixture (6) of one or more beneficial agents represented by dots (4) and lyotropic liquid crystals represented by wavy lines (5) is contained within the surrounding coating (3).

Figure 3:
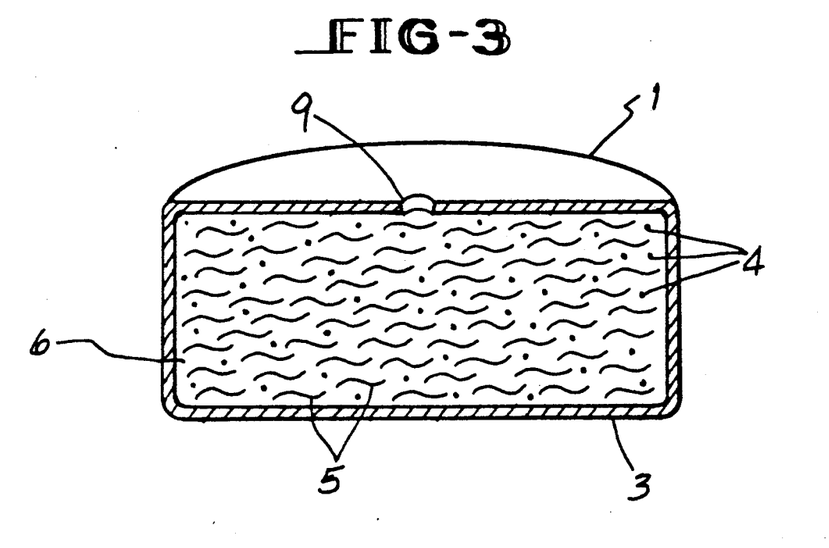
FIG. 3 is a cross-sectional view through the axis of another embodiment of the device (1) of this invention wherein the device (1) is in the shape of a tablet and the coating contains a hole (9) through the coating on one face.

FIG. 3 is a cross-sectional view through the axis of another embodiment of the device (1) of this invention wherein the device (1) is in the shape of a tablet. The device (1) contains a hole (9) through the coating (3) on one face of the device (1). Within the surrounding coating (3) is a mixture (6) of one or more beneficial agents represented by dots (4) and lyotropic liquid crystals represented by wavy lines (5).

Figure 4:
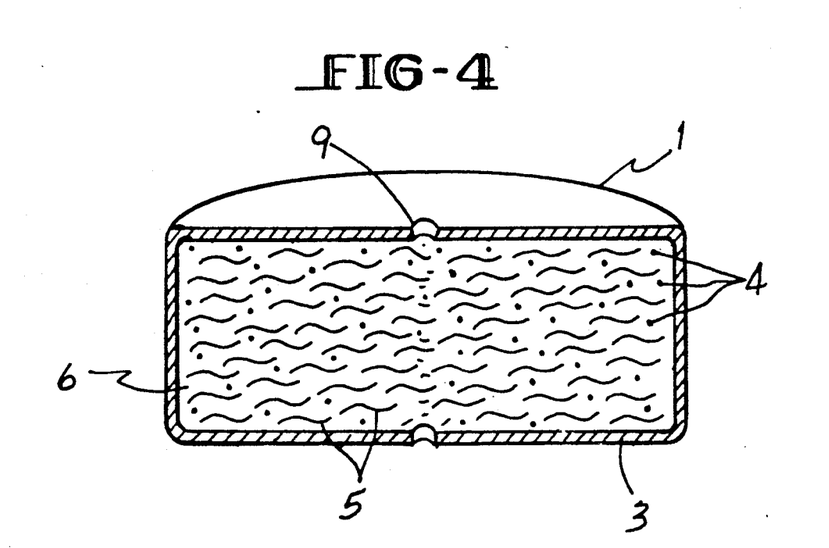
FIG. 4 is a cross-sectional view through the axis of another embodiment of the device (1) of this invention wherein the device (1) is in the shape of a tablet and the device contains a hole (9) through the entire device.

FIG. 4 is a cross-sectional view through the axis of another embodiment of the device (1) of this invention wherein the device (1) is in the shape of a tablet. The device (1) contains a hole (9) through the entire device (1). Within the surrounding coating (3) is a mixture (6) of one or more beneficial agents represented by dots (4) and lyotropic liquid crystals represented by wavy lines (5).

Figure 5:
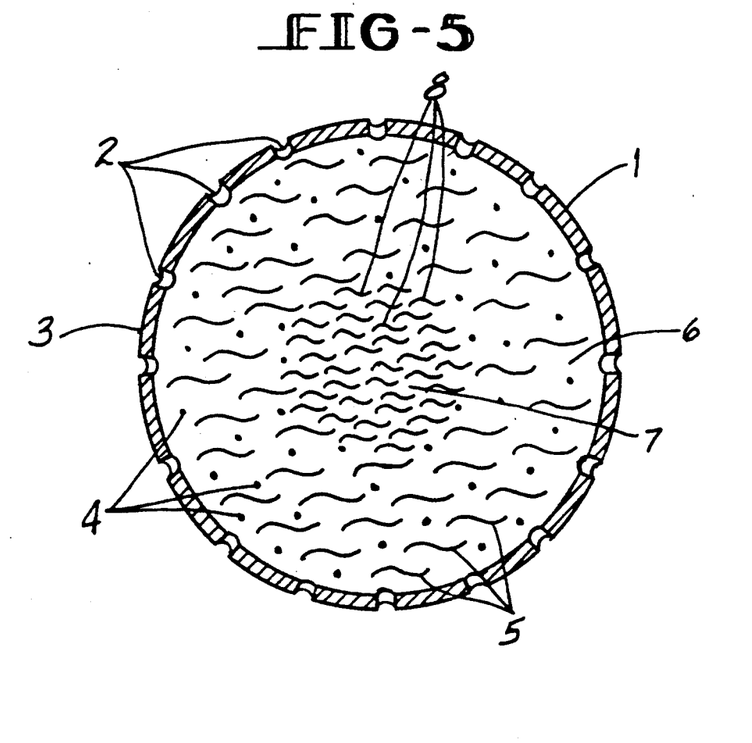
FIG. 5 is a cross-sectional view through the axis of another embodiment of the device (1) of this invention wherein the device (1) is a sphere or is substantially spherical in shape and which comprises two-layers (6 and 7) within the surrounding coating (3) of the device (1).

FIG. 5 is a cross-sectional view through the axis of another embodiment of the device (1) of this invention wherein the device (1) is a sphere or is substantially spherical in shape. The device (1) contains a plurality of pores (2) in and through the coating (3). Within the surrounding coating (3) are two layers (6 and 7). The outermost layer (6) comprises a mixture of one or more beneficial agents represented by dots (4) and lyotropic liquid crystals represented by wavy lines (5) and the innermost layer (7) comprises lyotropic liquid crystals represented by wavy lines (8) which can be the same or different than the lyotropic liquid crystals (5) of the outermost layer (6).

Figure 6:
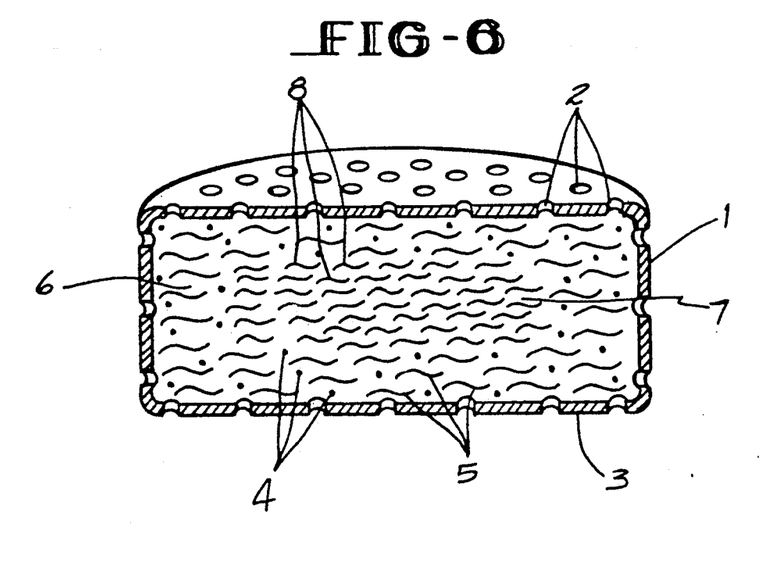
FIG. 6 is a cross-sectional view of another embodiment of the device (1) which is taken along line 2—2 of the device (1) shown in FIG. 1 which comprises two layers (6 and 7) within the surrounding coating (3) of the device (1).

FIG. 6 is a cross-sectional view of another embodiment of the device (1) shown in FIG. 1 which view is taken along line 2—2 of FIG. 1 and which device (1) comprises two layers (6 and 7) within the surrounding coating (3). The coating (3) contains a plurality of pores (2) in and through the coating (3). Contained within the surrounding coating (3) are an outermost layer (6) which comprises a mixture of one or more beneficial agents represented by dots (4) and lyotropic liquid crystals represented by wavy lines (5) and an innermost layer (7) which comprises lyotropic liquid crystals represented by wavy lines (8) which can be the same or different than the lyotropic liquid crystals (5) of the outermost layer (6).

Figure 7:
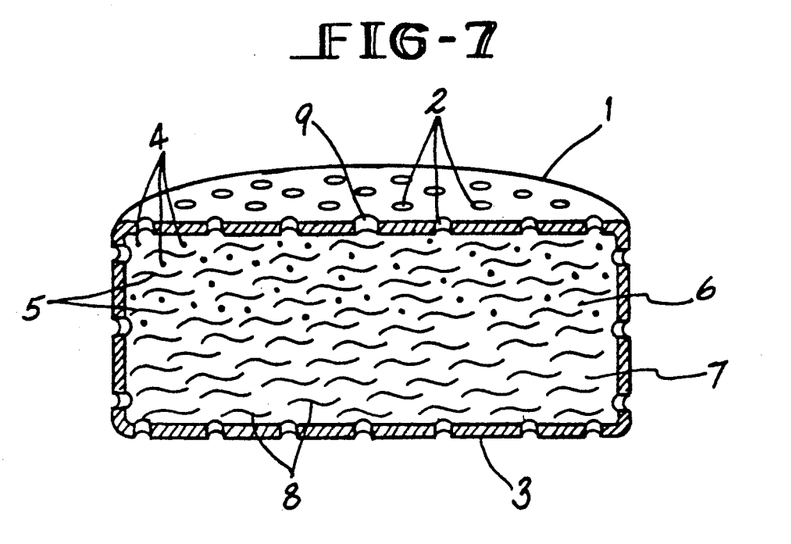
FIG. 7 is a cross-sectional view of another embodiment of the device (1) in the shape of a tablet which comprises two layers (6 and 7) within the surrounding coating (3) of the device (1) and which contains a hole through the coating (3) adjacent to layer (6) and a plurality of pores (2).

FIG. 7 is a cross-sectional view through the axis of another embodiment of the device (1) of this invention wherein the device (1) is in the shape of a tablet. The device (1) contains a hole (9) through the coating (3) on the face adjacent to the layer (6) which comprises a mixture of one or more beneficial agents represented by dots (4) and lyotropic liquid crystals represented by wavy lines (5). The coating (3) also contains a plurality of pores (2). Adjacent to layer (6) and having an area in contact therewith is another layer (7) which comprises lyotropic liquid crystals represented by wavy lines (8) which crystals are of the same or different composition as those of layer (6). Coating (3) surrounds the layers (6 and 7).

Figure 8:
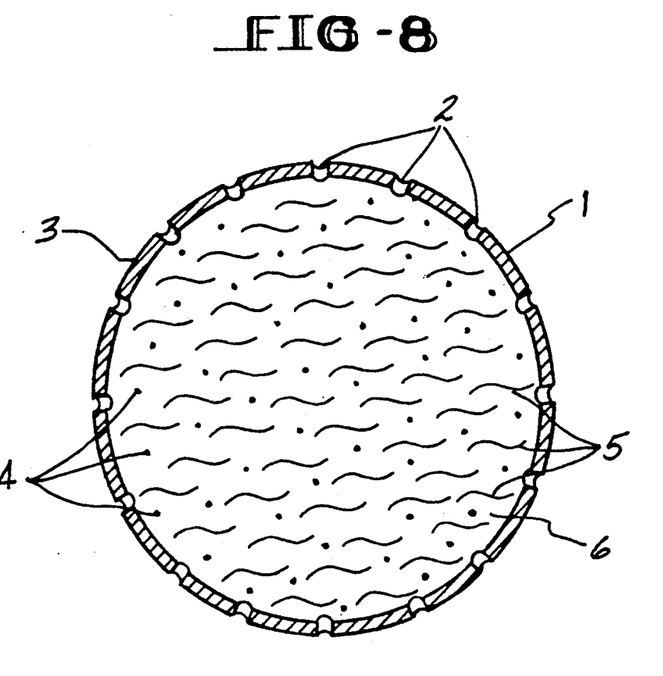
FIG. 8 is a cross-sectional view through the axis of another embodiment of the device (1) of this invention wherein the device (1) is a sphere or is substantially spherical in shape.

FIG. 8 is a cross-sectional view through the axis of another embodiment of the device (1) of this invention wherein the device is a sphere or is substantially spherical in shape. The device (1) contains a plurality of pores (2) in and through the coating (3). Within the surrounding coating (3) is a mixture (6) of one or more beneficial agents represented by dots (4) and lyotropic liquid crystals represented by wavy lines (5).

DETAILED DESCRIPTION OF THE INVENTION

This invention relates to devices powered by lyotropic liquid crystals for the controlled delivery of one or more beneficial agents to an environment of use.

The lyotropic liquid crystals employed in the various embodiments of the devices of this invention are comprised of those non-polymeric compounds, generally in the approximate molecular weight range 200–1500, also known in the art as amphipathic compounds, which form mesophases which swell in the presence of water. Examples of such mesophases are commonly known as lamellar, hexagonal and cubic mesophases. Compounds which form such lyotropic liquid crystals include natural phosphatides such as phosphatidylcholine (lecithin), phosphatidylethanolamine, phosphatidylserine, phosphatidylglycerol, phosphatidylinositol, phosphatidic acid, lysophosphatidylcholine, sphingomyelin and the like. Other lyotropic liquid crystal forming compounds include glycolipids such as monoglucosyldiglyceride, diglucosyldiglyceride, monogalactosidyldiglyceride, digalactosidyldiglyceride, glucosylceramide, galactosylceramide, lactosylceramide and the like. Still other compounds which form lyotropic liquid crystals within the scope of this invention include synthetic analogs of phosphatides and glycolipids such as N-methyl-phosphatidylethanolamine, N-succinyl-phosphatidylethanolamine, phospholipids with ether-linked hydrocarbon chains and alkyl-glycosides.

Still further, lyotropic liquid crystal forming compounds of this invention include the salts of fatty acids such as potassium or sodium salts, half-ionized fatty acid-salts, and synthetic detergents such as sodium dodecyl sulfate and the like.

Also within the scope of this invention are lyotropic liquid crystals which are comprised of mixtures of amphipathic compounds. By employing such mixtures, a further optimization, above that achieved through the selection of a particular amphipathic compound, of the desired properties of the swelling lyotropic liquid crystal phase is possible. For example, incorporation of charged fatty acids into zwitterionic phosphatidylcholine bilayers results in an increase in swelling capacity as has been described by Gulik-Krzywicki; et al., Mol. Cryst. Liq. Cryst. 8: 285-291 (1969). Further, mixtures of fatty acid salts and fatty alcohols such as potassium oleate and decanol can form swelling lyotropic liquid crystalline phases. Other examples of such mixtures are described by D. M. Small in *The Physical Chemistry of Lipids, Handbook of Lipid Research,* Vol. 4, Plenum Press, 1986, the teachings of which are incorporated herein by reference.

In the two layer embodiments of the devices of this invention, such as those shown in FIGS. 5, 6 and 7, the lyotropic liquid crystals of each layer may be the same or may be different. However, in the two layer embodiments of the devices of this invention wherein the coating in addition to one or more holes, or instead thereof, contains a plurality of pores, such as the embodiment shown in FIG. 7, it is preferred that the lyotropic liquid crystals (8) of layer (7) be of a higher molecular weight than the lyotropic liquid crystals (5) of layer (6). Still more preferably, the lyotropic liquid crystals (8) of such an embodiment should be of a sufficiently high molecular weight that substantially none of the lyotropic liquid crystals (8) is capable of leaving the device (1) through the pores (2). Nonetheless, since certain lyotropic liquid crystals increase in viscosity as a function of increase in molecular weight, the lyotropic liquid crystals (5) and (8) must be chosen or mixed such that they provide sufficient swelling properties but do not cause the device to burst. Selection of the appropriate lyotropic liquid crystals (8) for such devices is within the skill of those who practice in the relevant art enabled by the disclosure herein.

In addition to the lyotropic liquid crystals, the devices of this invention may optionally contain an osmotically effective solute for the purpose of providing a colloidal osmotic pressure which is additive with the swelling pressure of the lyotropic liquid crystals. Examples of osmotically effective solutes are inorganic and organic salts, and sugars. A preferred composition range for devices comprising such solutes is 0-30 wt % osmotically effective solute. Of course, for the devices of this invention which are to be employed to deliver a drug to an animal, any such solute must be pharmaceutically acceptable.

The devices of this invention comprise, in addition to the lyotropic liquid crystals described above and, optionally, an osmotically effective solute, one or more beneficial agents. The term beneficial agents as used in this specification and the accompanying claims includes, by way of example and not of limitation, any physiologically or pharmacologically active substance that produces a localized or systemic effect in animals. The term animals is meant to include mammals including human beings as well as other animals. The physiologically or pharmacologically active substance of this invention need not be soluble in water. Indeed, an advantage of the devices of this invention is that such insoluble or partially insoluble substances as well as soluble substances can be delivered to the environment of use in a controlled fashion by the devices hereof.

Examples of active substances employed in the devices of this invention include, without limitation, inorganic and organic compounds such as drugs that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretary systems, inhibitors of autocoids and histamine systems. The drug that can be delivered for acting on these systems includes anti-depressants, hypnotics, sedatives, psychic energizers, tranquilizers, anti-convulsants, muscle antisecretoric relaxants, anti-parkinson agents, analgesics, anti-inflammatory agents, local anesthetics, muscle contractants, antibiotics, anti-microbials, anthelmintics, anti-malarials, hormonal agents, contraceptives, histamines, antihistamines, adrenergic agents, diuretics, antiscabiosis, anti-pediculars, anti-parasitics, anti-neoplastic agents, hypoglycemics, electrolytes, vitamins, diagnostic agents and cardiovascular drugs. Also included in such active substances are prodrugs of the above-described drugs. Such drugs or prodrugs can be in a variety of forms such as the pharmaceutically acceptable salts thereof. However, a particular advantage of the devices of this invention is that such beneficial agents, such as the drugs and prodrugs described above, need not be soluble in water in order for the devices of this invention to deliver, in a controlled manner, such agents. It is within the scope of this invention that the devices can contain more than one beneficial agent.

Devices of this invention are particularly advantageous for delivering two or more drugs simultaneously. The rate of drug release is controlled primarily by the extrusion rate of the lyotropic liquid crystals and is relatively independent of the solubility of the incorporated drugs. Thus, two or more incorporated drugs will be released at absolute rates which depend upon their individual loadings in the device. For example, devices of the current invention can be used to co-deliver a sustained dose of an α-blocker, such as prazosin, and a diuretic, such as polythiazide, for the treatment of hypertension. For the treatment of cold symptoms, devices of this invention can be used to deliver a combination of a decongestant, such as pseudephedrine hydrochloride, and an antihistamine, such as chlorpheniramine maleate. For treatment of cough/cold symptoms, three or more drugs can be released in a controlled fashion from a device of this invention; for example a combination of an analgesic, a decongestant, an antihistamine, and an antitussive can be delivered. Those skilled in the art will recognize that the current invention can be used to provide controlled and sustained delivery of a wide variety of combinations of drugs.

The beneficial agents of this invention also include other substances for which it is desirable and/or advantageous to control delivery into an environment of use.

Examples of such substances include, but are not limited to, fertilizers, algacides, reaction catalysts and enzymes.

The devices of this invention also comprise a coating (3) which surrounds the mixture (6) of one or more beneficial agents (4) and lyotropic liquid crystals (5) or, in the two layer embodiments hereof, which surrounds both layers (6 and 7) except for the area in contact between such layers. The coating (3) comprises at least one water permeable polymer but, significantly and in contrast to many prior art devices, the coating need not be semi-permeable. Therefore, the coating (3) can be freely permeable to low molecular weight compounds. By way of example and not of limitation, such polymers for the coating (3) include cellulose acetate, ethylcellulose, silicone rubber, cellulose nitrate, polyvinyl alcohols, cellulose acetate butyrate, cellulose succinate, cellulose laurate, cellulose palmitate and the like. For example, suitable coatings are obtained with cellulose acetate having an average molecular weight of 40K or 60K. Also suitable for the coating (3) of the devices of this invention are biodegradable polymers which do not degrade significantly (i.e., break or burst) during the delivery period. Examples of such biodegradable polymers include polylactic acid, polyglycolic acid and poly(lactide-coglycolide). A preferred polymer for the coating (3) is cellulose acetate.

The coating (3) can also comprise one or more porosigens such that, when the devices of this invention are placed in an environment of use, said porosigen(s) dissolve and effect the formation of a plurality of pores (2) in and through the coating (3).

As stated above, the porosigens can be employed alone or in combination to effect formation of the pores (2) in and through the coating (3). The ratio of porosigen or porosigens to coating polymer can be varied as well as the choice of porosigens to be employed. Such variations are within the skill of those who practice in the art and will be determined by such factors as the solubility of the beneficial agent(s), the particle size of the agent(s), the molecular weight of the lyotropic liquid crystals and the desired rate of release. Examples of porosigens which will function to form the pores (2) in and through the coating (3) include inorganic salts such as sodium chloride, potassium chloride, potassium phosphate and the like. Other effective porosigens are certain particulate organic compounds and salts thereof such as glucose, sucrose, lactose, succinic acid, sodium succinate, sodium carbonate and the like. Also effective porosigens are water-soluble polymers such as polyethyleneglycol (PEG), methyl cellulose, hydroxypropylmethyl cellulose, hydroxypropyl cellulose (HPC), polyethylene oxide (PEO) and the like. Such pore-forming polymers must, however, have the ability to form a phase-separated coating when mixed with the coating forming polymer of this invention. That is to say, the porosigen polymer and the coating polymer cannot be totally miscible. Combinations of porosigens such as particulate organic compounds and salts thereof with inorganic salts and/or water-soluble polymers can be employed and are within the scope of this invention. Similarly inorganic salts with water-soluble polymers can be employed as porosigens in the devices of this invention. When the devices of this invention are to be used to deliver beneficial agents to an animal, the porosigen or porosigens employed must be pharmaceutically acceptable.

In addition to the formation of pores (2) upon placement of the devices of this invention into an environment of use through dissolution of one or more porosigens, the pores (2) can be preformed. Such preformed pores can be produced by methods well known to those skilled in the art such as by gas generation in the coating (3) during formation of the coating (3); etched nuclear tracking; laser, sonic or mechanical drilling; or electric discharge. It is preferred, however, that such pores result from dissolution of porosigen(s) as described above.

In addition to the pores described above, or instead thereof, the coating can contain one or more holes. The holes may extend through only the coating on one face of the device or extend through the entire device. However, it is preferred that in the two layer embodiments of the devices of this invention such as shown in FIG. 7, such holes do not extend through the entire device but only extend through the coating adjacent to the layer comprising the beneficial agent. Such holes are made by standard methods known to those skilled in the art such as by mechanical, sonic or laser drilling.

In addition to the above-mentioned components of the devices of this invention, other common pharmaceutical excipients may be present. Examples of such excipients include, but are not limited to, binders such as microcrystalline cellulose, plasticizers such as polyethyleneglycol-600, and buffers such as sodium phosphate.

The devices of this invention can be prepared in a variety of sizes and shapes. The particular size and shape of the device will be determined, in part, by the particular use to which the device is to be put. For example, for oral administration of a drug, the device of this invention can be in the shape of a tablet or caplet, is of suitable size for containing the desired dosage of drug and is capable of oral administration. Other shapes of the devices of this invention include, by way of example and not of limitation, cylindrical or conical shapes suitable for administration of drugs intravaginally and/or rectally and concave/convex shaped devices for ocular administration of drugs.

The devices of this invention can also be administered within a capsule comprising a water soluble wall. For example, the devices of this invention can be manufactured to be of suitable size for inclusion either singly or multiply within a gelatin capsule such that when the capsule dissolves the device or devices are released into the environment of use. While the devices to be included within a capsule can be of a variety of shapes, a preferred embodiment for such devices is spherical or substantially spherical. The exact number and size of such devices can and will be determined according to a variety of factors well known to those skilled in the art. For example, the environment of use, the beneficial agent or agents, the amount of beneficial agent and the rate of release are all factors to be considered in determining the size, shape and number of devices to be included in such capsules as well as the composition of the capsule.

While the actual process used to manufacture the devices of this invention may vary, one such preferred process is described below. The desired lyotropic liquid crystals are blended according to standard methods well known to those skilled in the art in a predetermined ratio (e.g. weight percent) with one or more beneficial agents (4) and any excipients and/or osmotically effective solute(s). The ratio used will vary to a greater or lesser degree depending upon the particular lyotropic liquid crystals, the particular beneficial agent(s) used and the release rate to be achieved. Generally, however, the devices of this invention will comprise lyotropic liquid crystals in an amount from about 50 to about 95 weight percent based on the total weight of the mixture (6) of lyotropic liquid crystals (5) and beneficial agent(s) (4), and any excipients and/or osmotically effective solute(s). The lyotropic liquid crystals (5) can comprise more than one amphipathic compound in which case all such amphipathic compounds are blended with the beneficial agent(s) (4) and any excipients and/or osmotically effective solute(s) either sequentially or simultaneously. Optionally and preferably, the lyotropic liquid crystals are sieved to a desired mesh cut prior to blending. If the desired device is to comprise one layer of the blended mixture (6) such as is shown in FIG. 2, then the resulting blended mixture (6) is pressed into the desired shape such as a tablet or caplet using a conventional tableting press such as a Kilian LX-21 rotary tablet press (Kilian and Co., Koln, Germany) according to conditions known to those skilled in the art.

Spherical or substantially spherical embodiments such as depicted in FIGS. 4 and 8 can be prepared in a variety of ways known to those skilled in the art. In a preferred method such embodiments are prepared using a Fuji extruder/spheronizer (Fuji Paudal Co., Tokyo, Japan) according to methods well known to those skilled in the art. When concentrically arranged embodiments are desired, lyotropic liquid crystal core beads are first prepared. These lyotropic liquid crystal beads then can be coated with a lyotropic liquid crystal/drug mixture using a Freund CF-granulator (CF-360, Freund Industrial Co., Tokyo, Japan) or a Glatt GPCG coating apparatus (Glatt Air Techniques, Ramsey, N.J.).

Following formation of the desired shape in the press, coating (3) is applied to the entire surface of the mixture (6), or the surface of layers (6) and (7) which are not in contact with each other, or the outer surface of the outermost layer (6) of the concentric embodiment such as depicted in FIG. 5. The coating (3), which also can comprise porosigen(s), is applied to the mixture or the outermost layer (6) or layers (6) and (7) according to standard methods well known to those skilled in the art. For those devices which are not spherical or substantially spherical, it is preferred that such coating be applied by spraying using, for example, a Freund Model HCT-30 Hicoater (Freund Industrial Co., Tokyo, Japan). For those devices which are spherical or substantially spherical, it is preferred that such coating be applied using, for example, a Freund CF-granulator or a Glatt GPCG coating apparatus as described above. As an example, when cellulose acetate is employed for the coating, it can be sprayed as an acetone solution (5%) or as other solutions such as in acetone/methanol (9:1). Such cellulose acetate coatings from acetone/methanol solution do result in a more opaque coating but have little or no observable impact on the functioning of the devices of this invention. The amount of coating (3) to be applied can be varied to affect the release rate of the devices but will generally be from about 4 to 50 weight percent of the total device weight with a range of from about 6 to 50 weight percent for those coatings (3) comprising porosigen(s).

For devices (1) of this invention which contain coating (3) in which the plurality of pores (2) is formed by means other than dissolution of porosigen(s), then a preferred amount of coating (3) is in the range of from about 6 to 25 weight percent with an even more preferred range being from about 8 to 20 weight percent. If such coating (3) contains porosigen(s), then a preferred amount of coating (3) for the devices (1) of this invention is a range of from about 8 to 30 weight percent with an even more preferred range being from about 10 to 25 weight percent.

If the coating (3) contains one or more porosigens, then the pores (2) will be formed in situ when the device (1) is placed in the environment of use. Of course, while not necessarily advantageous, the pores (2) of such devices can be preformed by placing the device first into a suitable aqueous environment then, upon dissolution or partial dissolution of the porosigen(s), into the environment of use.

If the coating (3) does not contain any porosigen, then the pores (2) can be formed by other methods well known to those skilled in the art. For example, pores (2) in coating (3) can be formed by gas generation during formation of the coating (3) following application of the coating mixture to the device. Other processes to produce pores (2) in coating (3) include the use of etched nuclear tracking, the use of laser, sonic or mechanical drilling and the use of electrical discharge. Additionally, in coatings without porosigens, pores can be formed in the environment of use by bursting of weak portions of the membrane as a result of the internal pressure generated by the interior swelling lyotropic liquid crystals.

A combination of the above described methods for producing pores (2) in coating (3) can be employed and are within the skill of those skilled in the art enabled by the disclosure herein. Such devices are within the scope of this invention.

When employing porosigens to form the pores (2) in coating (3), particular attention is to be paid to the beneficial agent or agents to be delivered by the device (1). If the beneficial agent is soluble, then pore size is not as crucial as when the agent is insoluble. Indeed, the devices of this invention will function to controllably release certain agents even though the pore size is less than 0.1 micron where such agent is soluble. However, where delivery of an insoluble agent, such as the drug glipizide, is desired, then the porosigen employed must be such that, upon dissolution, pores (2) having diameters greater than the particle size of the agent are formed in and through the coating (3). For example, sucrose of a selected mesh cut can be employed in a suspension comprising cellulose acetate to form a coating (3) which, upon subsequent dissolution of the sucrose, will yield pores (2) of a preselected (i.e., mesh cut) size. Similarly, commercially available sucrose beads can be so employed. For certain beneficial agents and/or environments of use, it may be advantageous or preferable to include more than one porosigen. For example, coating mixtures which comprise coating polymer, water soluble polymer and sucrose such as cellulose acetate/polyethylene glycol-600 (1:1) with 50% particulate sucrose can be suitably employed. The choice of porosigen or porosigens as well as the amount thereof employed in the coating mixture can be readily determined by those skilled in the art enabled by this disclosure.

Similarly, when the pores (2) in coating (3) are formed by means other than by dissolution of porosigen(s), the nature of the beneficial agent(s) to be delivered by the device (1) must be considered to insure that the pores (2) are of sufficient diameter as described above. Formation of pores (2) of varying diameter according to the methods described above are well known to those skilled in the art.

When the devices of this invention are to contain one or more holes in the coating (3) or through the device (1), then, after such devices have been coated as described above, the desired number and size holes are drilled through the coating or device according to standard methods such as mechanical, sonic or laser drilling.

Methods for using the devices of this invention include administration of the appropriate devices to animals via oral administration or by insertion of the appropriate devices into a body cavity of the animal. Devices of this invention can also be used to deliver agents to such environments of use as fish tanks, soil and aqueous chemical and/or enzymatic reaction systems. In such cases, the devices are placed into the desired environment of use. The devices of this invention require that any such environment of use be either aqueous or provide for contact of the device with water or other aqueous medium.

The following examples will serve to illustrate the devices of this invention and are not to be construed as limiting the scope hereof to those embodiments specifically exemplified.

EXAMPLE 1

Finely milled (approximately 100/200 mesh) Alcolec lecithin (FF-100, American Lecithin Co., Atlanta, Ga.), mixture of soybean phospholipids) was blended with 5 weight percent of the insoluble drug glipizide and 2 weight percent silica (CAB-O-SIL; Cabot Corp., Tuscola, Ill.), an anticaking agent. Tablets of 500 mg each were prepared by direct compression in a Carver press at a force of 1 metric ton for 2 seconds. The tablets were spray coated by standard methods with an acetone solution of 1:1 (w/w) cellulose acetate/PEG-600 to a final coating level of 12.7 weight percent. Then, a single hole (1.07 mm diameter) was drilled through the coating in the center of one face of the tablets using a bench-top drill press (Cameron Precision Engineering Co., model 164C-7).

EXAMPLE 2

Following the procedure of Example 1, 500 mg tablets were prepared and then coated with an acetone solution of 4:1 (w/w) cellulose acetate/PEG-600 to a final coating level of 11.3 weight percent. A single hole (1.07 mm diameter) was drilled through the coating in the center of one face of the tablets as described in Example 1.

EXAMPLE 3

Following the procedure of Example 2, coated lecithin/glipizide tablets (500 mg) were prepared. Then, the tablets were drilled to produce either one, three or six holes (1.07 mm diameter) through the coating on one face of the tablets. The coating level of the tablets was determined to be 11.9 weight percent.

EXAMPLE 4

Following the procedure of Example 2, coated lecithin/glipizide tablets (500 mg) were prepared with the exception that various coating levels were applied. Using standard spray coating methods, the tablets were coated to levels of 7.7 wt. %, 11.9 wt. %, 15.5 wt. % or 19.1 wt.%. Then, one hole was drilled as described in Example 1 through the coating in the center of one face of the tablets.

EXAMPLE 5

A blend comprising 73 wt % finely milled (approximately 100/200 mesh) Alcolec lecithin (FF-100; American Lecithin Co., Atlanta, Ga.), 20 wt % sucrose, 5 wt % glipizide and 2 wt % silica was prepared. Tablets (500 mg) were prepared from the blend by direct compression in a Carver press at a force of 1 metric ton for 2 seconds. The tablets were spray coated to a level of 11.7–11.9% from an acetone solution of 1:1 (w/w) cellulose acetate/PEG-600. Then, a single hole 1.07 mm diameter) was drilled through the coating in the center of one face of the tablets.

EXAMPLE 6

Finely milled (approximately 100/200 mesh) Alcolec lecithin (FF-100, American Lecithin Co., Atlanta, Ga.) was blended with 2 wt % silica (CAB-O-SIL, Cabot Corp., Tuscola, Ill.) and a 250 mg tablet was made by lightly compressing the blend on a lower 13/32 inch standard concave punch with a 13/32 inch flat upper punch by tapping the upper punch with a hammer. Then, without removing the tablet, the upper punch was removed and 250 mg of a blend comprising 88 wt % Alcolec lecithin, 10 wt % glipizide and 2 wt % silica was added to the press. Using an upper 13/32 inch standard concave punch, the tablet was compressed at 1 metric ton for 2 seconds. The resulting 500 mg bilayer tablet was spray coated to a level of 12.7 weight % with an acetone solution of 1:1 (w/w) cellulose acetate/PEG-600. Then, a single hole (1.07 mm diameter) was drilled through the coating in the center of the tablet face next to the glipizide containing layer using a bench-top drill press (Cameron Precision Engineering Co., model 164C-7).

EXAMPLE 7

Following the procedure of Example 6, bilayer tablets were prepared and then coated to a level of 11.1 weight % with an acetone solution of 4:1 (w/w) cellulose acetate/PEG-600. Then, a single hole (1.07 mm diameter) was drilled through the coating in the center of the tablet face next to the glipizide containing layer using a bench-top drill press (Cameron Precision Engineering Co., model 164C-7).

EXAMPLE 8

The release rates for the devices described in Examples 1–7 were determined according to the procedures described below. The device under study was placed in an individual well of a USP dissolution apparatus which well contained 1000 ml of 0.025M Tris.HCl, pH 7.5 as the release medium. The well containing the device was stirred at 100 rpm. Aliquots of the release medium were removed at various times, and a portion of each aliquot was diluted 1:1 (v/v) with methanol, in order to solubilize the lecithin. Glipizide was assayed by an HPLC assay using a 3.9 mm×15 cm Novapack $C_{18}$ column (Waters Associates, Milford, Mass.) with a mobile phase consisting of 50 volume percent 0.05M sodium phosphate, pH 7.5, and 50 volume percent methanol at a flow rate of 1.0 ml/min and detection at 227 nm. Employing the above described assay procedures, the devices of Examples 1–7 were assayed for release of the beneficial agent and the data is presented in Tables I to V below.

TABLE I

Percent of Glipizide Released over Time from Devices of Examples 1 and 2

| Time(hrs.) | Percent Glipizide Released | |
|---|---|---|
| | Device of Example 1 | Device of Example 2 |
| 0.00 | 0 | 0 |
| 0.07 | 0 | 0 |
| 1.63 | 9.2 | 3.6 |
| 3.17 | 18.3 | 8.6 |
| 4.70 | 22.4 | 13.4 |
| 6.23 | 28.3 | 17.8 |
| 7.77 | 32.0 | 22.4 |
| 9.30 | 36.9 | 26.1 |
| 10.83 | 40.4 | 29.4 |
| 12.37 | 42.8 | 30.2 |
| 13.90 | 49.1 | 31.0 |
| 15.43 | 50.4 | 32.2 |
| 18.16 | 56.8 | 34.6 |
| 19.75 | 56.2 | 35.0 |
| 21.25 | 56.4 | 35.9 |

Table I, above, shows that the devices coated with 1:1 (w/w) cellulose acetate/PEG-600 (Example 1) release glipizide, an insoluble drug, at a faster rate then the devices coated with 4:1 (w/w) cellulose acetate/PEG-600 (Example 2).

TABLE II

Percent of Glipizide Released over Time from Devices of Example 3

| Time(hrs.) | Percent Glipizide Released | | |
|---|---|---|---|
| | Device with One Hole | Device with Three Holes | Device with Six Holes |
| 0 | 0 | 0 | 0 |
| 1.0 | 0.95 | 1.29 | 1.45 |
| 2.0 | 3.96 | 5.34 | 5.23 |
| 3.0 | 6.99 | 8.27 | 10.43 |
| 4.0 | 10.09 | 11.16 | 14.54 |
| 5.0 | 13.36 | 13.81 | 18.12 |
| 6.0 | 16.28 | 16.06 | 20.87 |
| 7.0 | 18.28 | 18.27 | 22.27 |
| 8.0 | 20.18 | 20.75 | 24.24 |
| 9.5 | 24.36 | 23.78 | 25.03 |
| 11.0 | 27.45 | 27.01 | 30.16 |
| 12.5 | 28.64 | 29.00 | — |
| 14.0 | 28.53 | 31.19 | 32.76 |
| 15.5 | 31.40 | 32.54 | — |
| 17.0 | 31.52 | 33.51 | 38.75 |
| 17.67 | 31.88 | 33.89 | 38.85 |
| 19.16 | 33.02 | 34.42 | 40.64 |
| 21.16 | 34.58 | 35.57 | 42.8 |
| 23.16 | 36.09 | 37.26 | 45.1 |

Table II, above, shows the release of glipizide from devices of Example 3 as a function of the number of holes in the coating of the device.

TABLE III

Percent of Glipizide Released over Time from Devices of Example 4

| Time(hrs.) | Percent Glipizide Released | | | |
|---|---|---|---|---|
| | 7.7 wt % coating | 11.9 wt % coating | 15.5 wt % coating | 19.1 wt % coating |
| 0 | 0 | 0 | 0 | 0 |
| 1 | 1.29 | 0.95 | 0.92 | 0.74 |
| 2 | 5.34 | 3.96 | 3.20 | 2.98 |
| 3 | 8.27 | 6.99 | 6.23 | 5.93 |
| 4 | 11.16 | 10.09 | 9.39 | 8.30 |
| 5 | 13.81 | 13.36 | 12.16 | 10.68 |
| 6 | 16.06 | 16.28 | 14.40 | 12.70 |
| 7 | 18.27 | 18.28 | 16.44 | 14.94 |
| 8 | 20.75 | 20.18 | 18.90 | 16.94 |
| 9.5 | 23.78 | 24.36 | 21.88 | 19.82 |
| 11 | 27.01 | 27.45 | 24.63 | 23.33 |
| 12.5 | 29.00 | 28.64 | 27.38 | 25.90 |
| 14 | 31.19 | 28.53 | 27.82 | 28.32 |
| 15.5 | 32.54 | 31.40 | 29.47 | 29.65 |
| 17.0 | 33.51 | 31.52 | 30.49 | 30.81 |
| 17.67 | 33.89 | 31.88 | 30.84 | 30.99 |
| 19.16 | 34.42 | 33.02 | 32.12 | 33.14 |
| 21.16 | 35.57 | 34.58 | 32.81 | 33.68 |
| 23.16 | 37.26 | 36.09 | 34.25 | 34.28 |

Table III, above, shows that there is a minimal effect on release of glipizide from the devices of Example 4 due to varying coating levels among the levels tested.

TABLE IV

Percent of Glipizide Released over Time from Devices of Examples 1 and 5

| Time(hrs.) | Percent Glipizide Released | |
|---|---|---|
| | Device of Example 1 | Device of Example 5 |
| 0 | 0 | 0 |
| 0.07 | 0 | — |
| 1.0 | — | 9.96 |
| 1.63 | 9.2 | — |
| 2.0 | — | 20.31 |
| 3.0 | — | 29.40 |
| 3.17 | 18.3 | — |
| 4.0 | — | 38.12 |
| 4.7 | 22.4 | — |
| 5.0 | — | 42.60 |
| 6.0 | — | 47.92 |
| 6.23 | 28.3 | — |
| 7.0 | — | 50.74 |
| 7.77 | 32.0 | — |
| 8.0 | — | 55.66 |
| 9.0 | — | 58.92 |
| 9.30 | 36.9 | — |
| 10.0 | — | 62.36 |
| 10.83 | 40.4 | — |
| 11.0 | — | 62.53 |
| 12.37 | 42.8 | — |
| 12.5 | — | 64.30 |
| 13.9 | 49.1 | — |
| 14.0 | — | 63.54 |
| 15.43 | 50.4 | — |
| 18.16 | 56.8 | — |
| 19.75 | 56.2 | — |
| 21.25 | 56.4 | — |

Table IV, above, shows that the extend and rate of release of glipizide is increased when the osmotically effective solute sucrose is added to the mixture of the device of Example 1.

TABLE V

Percent of Glipizide Released over Time from Devices of Examples 6 and 7

| Time(hrs.) | Percent Glipizide Released | |
|---|---|---|
| | Device of Example 6 | Device of Example 7 |
| 0 | 0 | 0 |
| 0.07 | 0.3 | 0.1 |
| 1.63 | 17.1 | 5.4 |
| 3.17 | 33.3 | 15.8 |
| 4.70 | 49.1 | 25.8 |
| 6.23 | 58.2 | 33.4 |
| 7.77 | 60.4 | 41.0 |
| 9.30 | 63.7 | 49.0 |
| 10.83 | 71.6 | 49.8 |
| 12.37 | 71.6 | 51.3 |
| 13.90 | 70.8 | 53.6 |
| 14.43 | 72.3 | 55.6 |

TABLE V-continued

Percent of Glipizide Released over Time from Devices of Examples 6 and 7

| Time(hrs.) | Percent Glipizide Released | |
|---|---|---|
| | Device of Example 6 | Device of Example 7 |
| 18.16 | 74.8 | 56.3 |
| 19.75 | 74.9 | 57.1 |
| 21.25 | 75.5 | 60.9 |

Table V, above, shows that the bilayer devices coated with 1:1 (w/w) cellulose acetate/PEG-600 (Example 6) release glipizide at a faster rate than such devices coated with 4:1 (w/w) cellulose acetate/PEG-600 (Example 7). Comparing Table I and V, above, it is seen that release of glipizide from the bilayer devices of Examples 6 and 7 is at a faster rate than from the monolayer devices of Examples 1 and 2.

EXAMPLE 9

Uncoated lecithin/glipizide tablet cores are prepared as described in Example 1. These tablets are spray-coated with an acetone solution of cellulose acetate and hydroxypropylcellulose (1:1, w/w). Alternatively, the tablets are spray-coated with a suspension of sucrose (60/80 mesh) in an acetone solution of cellulose acetate (2.5 wt %) and PEG-600 (2.5 wt %). The final weight ratio of cellulose acetate, PEG-600, and sucrose is 1:1:2. The final coating level is 5-25 weight % of the coated tablet. The glipizide release kinetics are assessed as described in Example 8. These kinetics are used to optimize the rate and duration of drug release by further formulation changes, for example, changes in the lyotropic liquid crystal, the coating level, the coating composition, and by addition of other tablet excipients as will be obvious to those skilled in the art based on the disclosure herein.

EXAMPLE 10

Tablets providing a sustained release dose of an α-blocker/antihypertensive agent and a diuretic/antihypertensive agent are prepared as follows. Soybean lecithin is blended with prazosin hydrochloride and polythiazide in the ratio 476:20:4. This blend is compressed to form 500 mg tablets using a tablet press. These tablets are spray-coated with cellulose acetate plasticized with PEG-600, using an acetone solution of cellulose acetate and PEG-600, as described in Example 1. A single hole is drilled through the water-permeable cellulose acetate coating in the center of one face of each tablet. The release kinetics of the two drugs are assessed using methodology well known in the art. These kinetics are used to optimize the rate and duration of drug release by further formulation changes, for example: changes in the lyotropic liquid crystal, the coating level, the coating composition, and by addition of other tablet excipients as will be obvious to those skilled in the art based on the disclosure herein.

EXAMPLE 11

A muliparticulate liquid crystal/drug dosage form is prepared as follows. Glipizide and soybean lecithin are blended in the ratio 1:9. This blend is mixed with a small amount of solvent, e.g. water, in a Hobart mixer (Hobart Co., Troy, Ohio). The wet powder is transferred to a Fuji extruder (Fuji Paudal Co., Tokyo, Japan) and short (1 inch×1/16 inch) strands are formed. The extruded material is transferred to a Fuji spheronizer which transforms the material into beads of approximate diameter 0.5-1.5 mm. After drying, the beads are spray-coated in a Freund CF-granulator (CF-360; Freund Industrial Co., Tokyo, Japan) with an acetone solution of cellulose acetate and hydroxypropylcellulose (1:1, w/w). Alternatively, the drug/lecithin beads are spray-coated with a suspension of sucrose (preferably 100/200 mesh) in an acetone solution of cellulose acetate and PEG-600. The final weight ratio of cellulose acetate, PEG-600, and sucrose is 4:1:5; the final coat comprises 5-25 wt % of the coated bead. An amount of coated beads corresponding to the desired drug dose is filled into a gelatin capsule. The glipizide release kinetics are assayed as described in Example 8. These kinetics are used to optimize the rate and duration of drug release by further formulation changes, for example: changes in the lyotropic liquid crystal, the coating level, the coating composition, and by the addition of other excipients as will be obvious to those skilled in the art based on the disclosure herein.

What is claimed is:

1. A dispensing device for the controlled delivery of a beneficial agent comprising a drug or mixtures thereof which comprises:
   (a) an innermost layer comprising lyotropic liquid crystals;
   (b) an outermost layer adjacent to and surrounding the innermost layer and comprising a mixture of one or more beneficial agents and lyotropic liquid crystals; and
   (c) a water permeable polymer coating containing a plurality of pores which coating surrounds the outermost layer; wherein said controlled delivery is effected by swelling of said lyotropic liquid crystals.

2. The dispensing device according to claim 1 wherein the innermost layer additionally comprises an osmotically effective solute.

3. The dispensing device according to claim 1 wherein the outermost layer additionally comprises an osmotically effective solute.

4. The dispensing device according to claim 1 wherein the innermost and outmost layers each additionally comprise an osmotically effective solute.

5. The dispensing device according to claim 1 wherein the coating additionally contains at least one hole.

6. A dispensing device for the controlled delivery of a beneficial agent comprising a drug or mixtures thereof which comprises:
   (a) an innermost layer comprising lyotropic liquid crystals;
   (b) an outermost layer adjacent to and surrounding the innermost layer and comprising a mixture of one or more beneficial agents and lyotropic liquid crystals; and
   (c) a water permeable polymer coating which surrounds the outermost layer and which comprises a polymer and one or more porosigens; wherein said controlled delivery is effected by swelling of lyotropic liquid crystals.

7. The dispensing device according to claim 6 wherein the innermost layer additionally comprises an osmotically effective solute.

8. The dispensing device according to claim 6 wherein the outermost layer additionally comprises an osmotically effective solute.

9. The dispensing device according to claim 6 wherein the innermost and outermost layers each additionally comprise an osmotically effective solute.

10. The dispensing device according to claim 6 wherein the coating additionally contains at least one hole.

11. A dispensing device for the controlled delivery of a beneficial agent comprising a drug or mixtures thereof which comprises:
    (a) an innermost layer comprising lyotropic liquid crystals;
    (b) an outermost layer adjacent to and surrounding the innermost layer and comprising a mixture of one or more beneficial agents and lyotropic liquid crystals; and
    (c) a water permeable polymer coating containing at least one hole which coating surrounds the outermost layer; wherein said controlled delivery is effected by swelling of lyotropic liquid crystals.

12. The dispensing device according to claim 11 wherein the innermost layer additionally comprises an osmotically effective solute.

13. The dispensing device according to claim 11 wherein the outermost layer additionally comprises an osmotically effective solute.

14. The dispensing device according to claim 11 wherein the innermost and outermost layers each additionally comprise an osmotically effective solute.

15. A method for the controlled delivery of one or more beneficial agents to an environment of use which comprises placing the device of claim 1 into the environment of use.

16. A method for the controlled delivery of one or more beneficial agents to an environment of use which comprises placing the device of claim 6 into the environment of use.

17. A method for the controlled delivery of one or more beneficial agents to an environment of use which comprises placing the device of claim 11 into the environment of use.

18. A capsule which comprises a water soluble wall and one or more devices of claim 6.

19. A method for the controlled delivery of a drug to an animal which comprises administering to the animal the device according to claim 18 wherein the beneficial agent is a drug.

* * * * *